(12) United States Patent
El-Baz et al.

(10) Patent No.: US 11,534,064 B2
(45) Date of Patent: Dec. 27, 2022

(54) SEGMENTATION OF RETINAL BLOOD VESSELS IN OPTICAL COHERENCE TOMOGRAPHY ANGIOGRAPHY IMAGES

(71) Applicants: University of Louisville Research Foundation, Inc., Louisville, KY (US); University of Massachusetts, Boston, MA (US)

(72) Inventors: Ayman El-Baz, Louisville, KY (US); Nabila Eldawi, Louisville, KY (US); Shlomit Schaal, Worcester, MA (US); Mohammed Elmogy, Louisville, KY (US); Harpal Sandhu, Louisville, KY (US); Robert S. Keynton, Goshen, KY (US); Ahmed Soliman, Louisville, KY (US)

(73) Assignees: University of Louisville Research Foundation, Inc., Louisville, KY (US); University of Massachusetts, Boston, MA (US)

( * ) Notice: Subject to any disclaimer, the term of this patent is extended or adjusted under 35 U.S.C. 154(b) by 0 days.

(21) Appl. No.: 16/620,496

(22) PCT Filed: Jun. 20, 2018

(86) PCT No.: PCT/US2018/038513
§ 371 (c)(1),
(2) Date: Dec. 7, 2019

(87) PCT Pub. No.: WO2018/237011
PCT Pub. Date: Dec. 27, 2018

(65) Prior Publication Data
US 2020/0178794 A1 Jun. 11, 2020

Related U.S. Application Data

(60) Provisional application No. 62/522,592, filed on Jun. 20, 2017.

(51) Int. Cl.
A61B 3/12 (2006.01)
G06T 7/143 (2017.01)
(Continued)

(52) U.S. Cl.
CPC ............ *A61B 3/1233* (2013.01); *G06T 5/002* (2013.01); *G06T 7/0012* (2013.01); *G06T 7/11* (2017.01);
(Continued)

(58) Field of Classification Search
CPC ..... A61B 3/102; A61B 3/1225; A61B 3/1233; A61B 3/1241; G06K 9/46;
(Continued)

(56) References Cited

U.S. PATENT DOCUMENTS

2015/0305614 A1 10/2015 Narasimha-Iyer et al.
2016/0242638 A1* 8/2016 Durbin .................. A61B 3/113
(Continued)

FOREIGN PATENT DOCUMENTS

WO 2016/109750 A1 7/2016

OTHER PUBLICATIONS

Paredes Soto, Daniel Alonso. Probabilistic labelling for enhancement of vessel networks applied to retinal images. Diss. University of Sheffield, 2016. (Year: 2016).*
(Continued)

*Primary Examiner* — Vikkram Bali
(74) *Attorney, Agent, or Firm* — Dentons Bingham Greenebaum LLP; Brian W. Chellgren

(57) ABSTRACT

Methods for automated segmentation system for retinal blood vessels from optical coherence tomography angiography images include a preprocessing stage, an initial segmentation stage, and a refining stage. Application of machine-learning techniques to segmented images allow for
(Continued)

automated diagnosis of retinovascular diseases, such as diabetic retinopathy.

17 Claims, 11 Drawing Sheets

(51) Int. Cl.
  *G06T 7/11* (2017.01)
  *G06T 5/00* (2006.01)
  *G06T 7/00* (2017.01)
  *G06V 10/40* (2022.01)

(52) U.S. Cl.
  CPC .............. *G06T 7/143* (2017.01); *G06V 10/40* (2022.01); *G06T 2207/10101* (2013.01); *G06T 2207/20012* (2013.01); *G06T 2207/20021* (2013.01); *G06T 2207/20081* (2013.01); *G06T 2207/20084* (2013.01); *G06T 2207/30101* (2013.01)

(58) Field of Classification Search
  CPC . G06T 2207/10101; G06T 2207/20012; G06T 2207/20021; G06T 2207/20081; G06T 2207/20084; G06T 2207/30041; G06T 2207/30101; G06T 5/002; G06T 5/007; G06T 7/0012; G06T 7/11; G06T 7/143
  See application file for complete search history.

(56) References Cited

U.S. PATENT DOCUMENTS

2016/0278627 A1  9/2016  Huang et al.
2017/0039412 A1  9/2017  Solanki et al.

OTHER PUBLICATIONS

S. W. Franklin, S. E. Rajan, Computerized screening of diabetic retinopathy employing blood vessel segmentation in retinal images, Biocybernetics and Biomedical Engineering 34 (2) (2014) 117-124.
Q. Mirsharif, F. Tajeripour, H. Pourreza, Automated characterization of blood vessels as arteries and veins in retinal images, Computerized Medical Imaging and Graphics 37 (78) (2013) 607-617.
C. Ding, Y. Xia, Y. Li, Supervised segmentation of vasculature in retinal images using neural networks, in: 2014 International Conference on Orange Technologies, 2014, pp. 49-52.
A. J. Frame, P. E. Undrill, M. J. Cree, J. A. Olson, K. C. McHardy, P. F. Sharp, J. V. Forrester, A comparison of computer based classification methods applied to the detection of microaneurysms in opthalmic fluorescein angiograms, Computers in Biology and Medicine 28 (3) (1998) 225-238.
M. Larsen, J. Godt, N. Larsen, H. Lund-Andersen, A. K. Sjlie, E. Agardh, H. Kalm, M. Grunkin, D. R. Owens, Automated detection of fundus photographic red lesions in diabetic retinopathy, Investigative Ophthalmology & Visual Science 44 (2) (2003) 761.
E. Moult, W. Choi, N. Waheed, M. Adhi, B. Lee, C. Lu, V. Jayaraman, B. Potsaid, P. Rosenfeld, J. Duker, J. Fujimoto, Ultrahigh-speed swept-source oct angiography in exudative amd, Ophthalmic Surgery Lasers and Imaging Retina 45 (6) (2014) 496-505.
Basak Kausik et al: "Probabilistic graphical modeling of speckle statistics in laser speckle contrast imaging for noninvasive and label-free retinal angiography", 2015 37th Annual International Conference of the IEEE Engineering in Medicine and Biology Society (EMBC), IEEE, Aug. 25, 2015 (Aug. 25, 2015), pp. 6244-6247, XP032811588, DOI: 10.1109/EMBC.2015.7319819.
L. Kuehlewein, M. Bansal, T. L. Lenis, N. A. Iafe, S. R. Sadda, M. A. B. Filho, T. E. D. Carlo, N. K. Waheed, J. S. Duker, D. Sarraf, Optical coherence tomography angiography of type 1 neovascularization in age-related macular degeneration, American Journal of Ophthalmology 160 (4) (2015) 739-748.e2.
T. S. Hwang, Y. Jia, S. S. Gao, S. T. Bailey, A. K. Lauer, C. J. Flaxel, D. J. Wilson, D. Huang, Optical coherence tomography angiography features of diabetic retinopathy, Retina (Philadelphia, PA.) 35 (11) (2015) 2371-2376.
T. E. de Carlo, A. Romano, N. K. Waheed, J. S. Duker, A review of optical coherence tomography angiography (octa), International Journal of Retina and Vitreous 1 (1) (2015) 5.
P. Liskowski, K. Krawiec, Segmenting retinal blood vessels with deep neural networks, IEEE Transactions on Medical Imaging 35 (11) (2016) 2369-2380.
F. Caliv, M. Aletti, B. Al-Diri, A. Hunter, A new tool to connect blood vessels in fundus retinal images, in: 2015 37th Annual International Conference of the IEEE Engineering in Medicine and Biology Society (EMBC), 2015, pp. 4343-4346.
A. Fathi, A. R. Naghsh-Nilchi, Automatic wavelet-based retinal blood vessels segmentation and vessel diameter estimation, Biomedical Signal Processing and Control 8 (1) (2013) 71-80.
Q. P. Lau, M. L. Lee, W. Hsu, T. Y. Wong, Simultaneously identifying all true vessels from segmented retinal images, IEEE Transactions on Biomedical Engineering 60 (7) (2013) 1851-1858.
U. T. Nguyen, A. Bhuiyan, L. A. Park, K. Ramamohanarao, An effective retinal blood vessel segmentation method using multi-scale line detection, Pattern Recognition 46 (3) (2013) 703-715.
G. Azzopardi, N. Strisciuglio, M. Vento, N. Petkov, Trainable {COSFIRE} filters for vessel delineation with application to retinal images, Medical Image Analysis 19(1) (2015) 46-57.
R. Kafieh, H. Rabbani, F. Hajizadeh, M. Ommani, An accurate multi-modal 3-d vessel segmentation method based on brightness variations on oct layers and curvelet domain fundus image analysis, IEEE Transactions on Biomedical Engineering 60 (10) (2013) 2815-2823.
M. U. Akram, S. A. Khan, Multilayered thresholding-based blood vessel segmentation for screening of diabetic retinopathy, Engineering with Computers 29 (2) (2013) 165-173.
K. Gopinath, J. Sivaswamy, T. Mansoori, Automatic glaucoma assessment from angio-oct images, in: 2016 IEEE 13th International Symposium on Biomedical Imaging (ISBI), 2016, pp. 193-196.
M. H. Suh, L. M. Zangwill, P. I. C. Manalastas, A. Belghith, A. Yarmo-hammadi, F. A. Medeiros, A. Diniz-Filho, L. J. Saunders, S. Yousefi, R. N. Weinreb, Optical coherence tomography angiography vessel density in glaucomatous eyes with focal lamina cribrosa defects, Ophthalmology (2016).
T. Iwanami, T. Goto, S. Hirano, M. Sakurai, An adaptive contrast enhancement using regional dynamic histogram equalization, in: 2012 IEEE International Conference on Consumer Electronics (ICCE), 2012, pp. 719-722.
C. Bouman, K. Sauer, A generalized gaussian image model for edge-preserving map estimation, IEEE Transactions on Image Processing 2 (3) (1993) 296-310.
A. El-Baz, G. Gimel'farb, Em based approximation of empirical distribu¬tions with linear combinations of discrete gaussians, in: 2007 IEEE International Conference on Image Processing, vol. 4, 2007, pp. IV-373-IV-376.
F. Khalifa, G. M. Beache, M. A. El-Ghar, T. El-Diasty, G. Gimel'farb, M. Kong, A. El-Baz, Dynamic contrast-enhanced mri-based early detection of acute renal transplant rejection, IEEE Transactions on Medical Imaging 32 (10) (2013) 1910-1927.
International Search Report and Written Opinion, PCT/US2018/038513, dated Nov. 1, 2018, Applicant: University of Louisville Research Foundation, Inc.
Orlando Jose Ignacio et al: "A Discriminatively Trained Fully Connected Conditional Random Field Model for Blood Vessel Segmentation in Fundus Images", IEEE Transactions on Biomedical Engineering, IEEE Service Center, Piscataway, NJ, USA, vol. 64, No. 1, Jan. 2017 (Jan. 2017), pp. 16-27, XP011637711, ISSN: 0018-9294, Doi: 10.1109/TBME.2016.2535311.
L. R. Dice, Measures of the amount of ecologic association between species, Ecology 26 (3) (1945) 297-302.

(56) References Cited

OTHER PUBLICATIONS

J. V. B. Soares, J. J. G. Leandro, R. M. Cesar, H. F. Jelinek, M. J. Cree, Retinal vessel segmentation using the 2-d gabor wavelet and supervised classification, IEEE Transactions on Medical Imaging 25 (9) (2006) 1214-1222.

Hjilsicoba H. 10. AHaJ114114neCICIA 0630p. MeTogm uncDposoro anann3a cocygnciofi CIICTeMbl 10.110BeKa. 063op aunepaTypm, Komi-HA-mem-Las' 011TI4Ka, 2013, T 37, N4. c. 512, 515-517, 529, non-official translation (N. Y. N. Ilyasova. "State-of-the-art review. Methods of the digital analysis of vascular system of the person. Review of literature", Computer optics).

Nabila Eladawi et al: "Automatic blood vessels segmentation based on different retinal maps from OCTA scans", Computers in Biology and Medicine., vol. 89, Aug. 7, 2017 (Aug. 7, 2017), pp. 150-161, XP055756949, US ISSN: 0010-4825, DOI: 10.1016/j.compbiomed. 2017.08.008.

Prentasic Pavle et al: "Segmentation of the fovea' microvasculature using deep learning networks", Journal of Biomedical Optics, SPIE, vol. 21, No. 7, Jul. 2016 (Jul. 2016), p. 75008, XP060072045, ISSN: 1083-3668, DOI: 10.1117/1.J130.21.7.075008.

Huazhu Fu et al: "Retinal vessel segmentation via deep learning network and fully-connected conditional random fields", 2016 IEEE 13th International Symposium on Biomedical Imaging (ISBI), Apr. 2016 (Apr. 2016), pp. 698-701, XP055470260, DOI: 10.1109/ISBI. 2016.7493362 ISBN: 978-1-4799-2349-6.

\* cited by examiner (a) (b) (c)

(d) (e) (f)

(a)  (b)  (c)

(d)  (e)  (f)

(a)          (b)          (c)

(d)          (e)          (f)

(a) (b) (c)

(d) (e) (f)

(a)            (b)

(c)

SEGMENTATION OF RETINAL BLOOD VESSELS IN OPTICAL COHERENCE TOMOGRAPHY ANGIOGRAPHY IMAGES

This application claims the benefit of U.S. provisional patent application Ser. No. 62/522,592, filed Jun. 20, 2017, for SYSTEM FOR SEGMENTATION OF RETINAL BLOOD VESSELS USING OPTICAL COHERENCE TOMOGRAPHY, incorporated herein by reference.

FIELD OF THE INVENTION

Methods for automated segmentation system for retinal blood vessels from optical coherence tomography angiography images include a preprocessing stage, an initial segmentation stage, and a refining stage. Application of machine-learning techniques to segmented images allow for automated diagnosis of retinovascular diseases, such as diabetic retinopathy.

BACKGROUND OF THE INVENTION

The retinal vasculature is an essential structure in the retina and has a high impact on the quality of human vision. Changes in blood vessels in the retina have close relationships with many systemic, metabolic, and hematologic diseases. The morphology of the retinal vasculature can be used to identify and classify the severity of some diseases. Its status is an essential diagnostic aid in ophthalmology. In addition, it allows patients to be treated in the early stages of a disease and before advanced and irreversible pathology has developed. Therefore, the segmentation and analysis of the retinal vasculature's features can assist the ophthalmologists in detecting these changes.

Blood vessel segmentation involves partitioning a digital image into blood vessel segments and background segments, and yields information about the location of blood vessels and variations in vessel diameter. However, the precise segmentation of the retinal blood vessels is considered a challenging task. This is because of the nature of the background, variety of vessel sizes, low contrast of images, and potential presence of pathologies, such as hemorrhages and microaneurysms. Most common segmentation techniques produce broken or disconnected segments. The segmentation of the retinal blood vessels from color and gray fundus images is not efficient, because of the low resolution of the extracted images. Furthermore, the fundus images do not provide detailed information about the blood vessels in different retinal layers and suffer from the lack of depth information. Threshold-based segmentation techniques produce significant errors with respect to similarities in gray levels between the blood vessels and the background. Region growing segmentation techniques are sensitive to the location of the seed point. Observation and manual measurement of blood vessel changes are very complex tasks that require highly trained persons. Therefore, a need exists for automatic systems to segment and diagnose the changes in the retinal blood vessels.

Retinal blood vessels can be extracted from several retinal imaging modalities to estimate the status of the retinal vascular network. These imaging modalities include color fundus imaging, fluorescein angiography (FA), and optical coherence tomography angiography (OCTA). OCTA uses laser light reflectance of the surface of moving red blood cells to depict blood vessels through different segmented regions of the eye. An OCTA scan of a patient's retina comprises multiple individual A-scans, which are compiled into a B-scan providing cross-sectional structural information. The technique uses multiple B-scans taken over a period of time to detect variations in the intensity and/or phase features of the OCT signal resulting from the movement of blood. OCTA can detect erythrocyte movement that allows direct visualization of blood vessels in vivo without the use of exogenous dyes. It is a non-invasive modality that demonstrates neovascularization and capillary abnormalities, which are critical in the detection and management of some diseases, such as diabetic retinopathy (DR).

SUMMARY

Disclosed herein is an automatic segmentation system for retinal blood vessels from OCTA images. The system segments blood vessels from superficial and deep retinal maps for normal and diabetic cases. Broadly, the system includes a first preprocessing stage of reducing the noise and improving the contrast of the OCTA images by using the Generalized Gauss-Markov random field (GGMRF) model and regional dynamic histogram equalization (RDHE) model. A second stage includes integrating three segmentation models to create an initial segmentation of retinal blood vessels, the models being the initial intensity model, the current intensity model, and the spatial higher order joint Markov-Gibbs random field (HO-MGRF) model. A third stage includes refining segmentation by extracting connected regions using a 2D connectivity filter. The proposed segmentation system was tested on 23 normal data sets and 24 data sets for diabetic patients. Three different metrics were used to evaluate the accuracy and robustness of the segmentation system, which are Dice similarity coefficient (DSC), absolute vessels volume difference (VVD), and area under the curve (AUC). The results on OCTA data sets (DSC=95.04±3.75%, VVD=8.51±1.49%, and AUC=95.20±1.52%) show the promise of this segmentation system.

The disclosed segmentation system may have multiple applications, including but not limited to, early diagnosis of DR, early diagnosis of glaucoma, early diagnosis of macular edema, early diagnosis of hypertensive retinopathy, early detection of age-related macular degeneration, analysis of blood vessels in different part of the body, measuring different biomarkers to indicate unnoticeable changes in the retina, and integration with other retinal modalities, such as OCT images, to assess the health of patients' eyes.

The disclosed segmentation system provides several advantageous features, including but not limited to (1) extracting the whole retinal vasculature network from OCTA images, which helps in the early diagnosis of many diseases; (2) integrating different image features to produce high accuracy results; (3) extracting different retina biomarkers from the segmented image, such as vessels density, foveal avascular zone area, and vessels bifurcations; (4) processing a new image modality for the retina (i.e., OCTA), which can provide more information about the retina and retinal blood flow than other modalities, such as fundus images; (5) utilizing OCTA, a non-invasive technology that does not require dye injection or special treatment; (6) extracting the vessels in different retinal maps, such as deep and superficial retinal maps in OCTA scans; and (7) providing the ability analyze depth information, unlike current segmentation technologies which mostly use fundus images, which lack the depth information that exists in the retina.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein is not necessarily intended to address every object described herein, and each embodiment does not necessarily include each feature described. Other forms, embodiments, objects, advantages, benefits, features, and aspects of the present invention will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

DETAILED DESCRIPTION OF THE PREFERRED EMBODIMENTS

Figure 1:
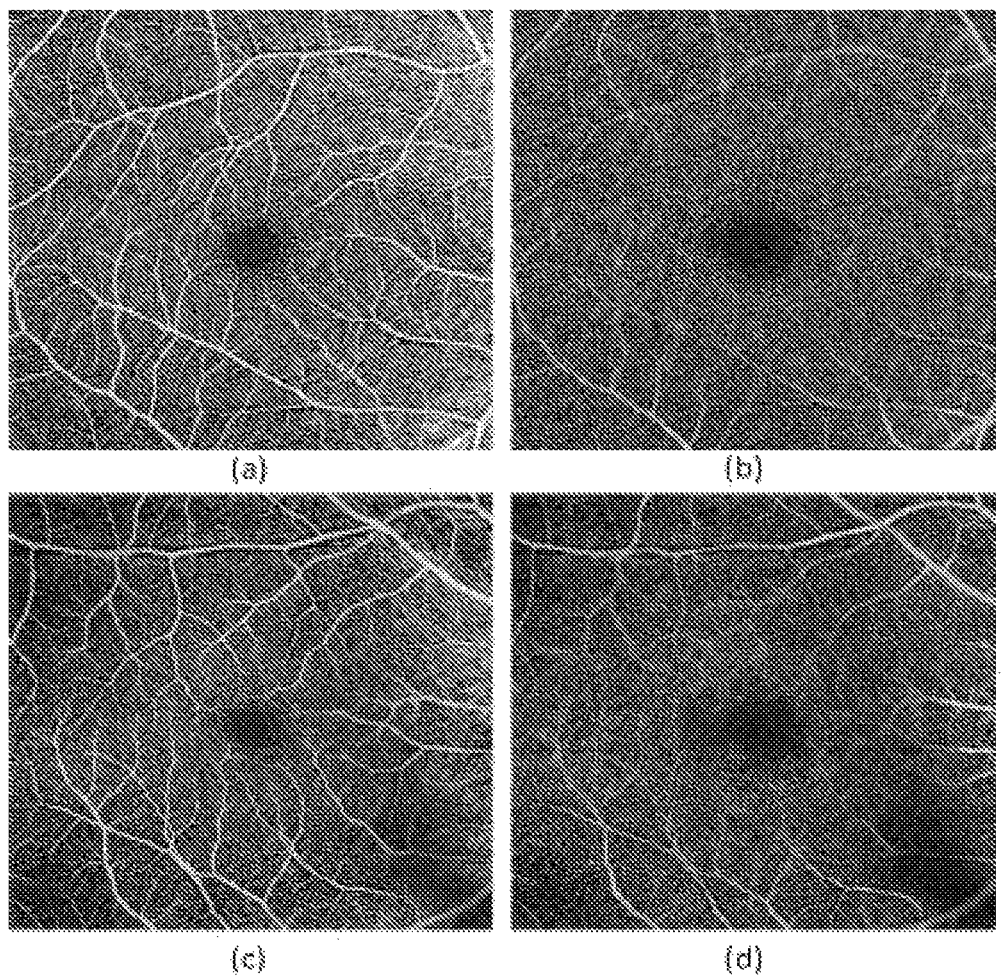
FIG. 1 depicts examples of OCTA images: (a) the superficial map for normal case, (b) the deep map for normal case, (c) the superficial map for mild DR case, and (d) the deep map for mild DR case.

For the purposes of promoting an understanding of the principles of the invention, reference will now be made to selected embodiments illustrated in the drawings and specific language will be used to describe the same. It will nevertheless be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to "advantages" provided by some embodiments of the present invention, other embodiments may not include those same advantages, or may include different advantages. Any advantages described herein are not to be construed as limiting to any of the claims.

Specific quantities (spatial dimensions, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

Mathematical notations used herein: Let $R=\{(i, j): 1 \leq i \leq I, 1 \leq j \leq J\}$ be a pixel location matrix of the image, $Q=\{1, 2, \ldots, Q\}$ be the gray levels' set in integer form, and $L=\{0, 1\}$ indicates a finite 2D arithmetic lattice that is upholding gray scale image and its blood vessels and background region maps. Let $g=\{g_{i,j}: (i, j) \in R, g_{i,j} \in Q\}$ and $m=\{m_{i,j}: (i, j) \in R, m_{i,j} \in L\}$ be a gray scale image taking values from Q, i.e., m: R→L, respectively.

FIG. 1 shows examples of retinal superficial (FIGS. 1A and 1C) and deep (FIGS. 1B and 1D) OCTA maps for both normal (FIGS. 1A and 1B) and DR (FIGS. 1C and 1D) cases. The retinal superficial map comprises a projection of the vasculature in the retinal nerve fiber layer (RNFL) and ganglion cell layer (GCL). The retinal deep map presents a composite of the vascular plexuses at two borders. The first is the border of inner nuclear layer (INL) and the outer plexiform layer (OPL). The second is the border of the inner plexiform layer (IPL) and INL.

The proposed blood vessel segmentation system is designed to extract the retinal vascular structure from OCTA scans automatically. Therefore, it can be analyzed and used as an indicator of systemic vascular and retinovascular diseases.

Figure 2:
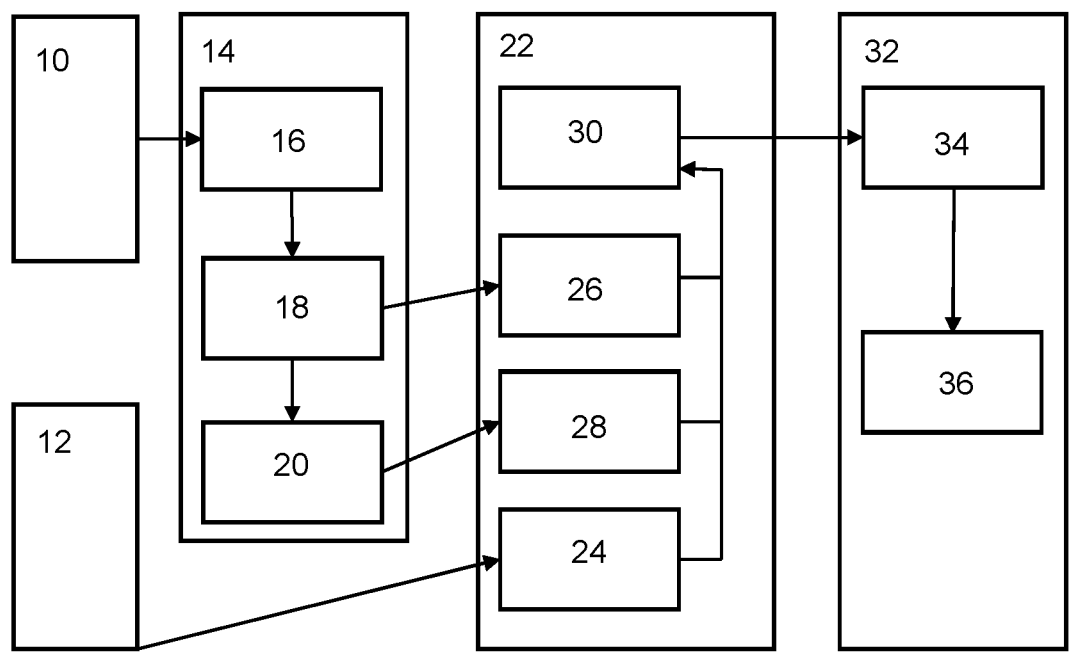
FIG. 2 is a schematic diagram depicting the proposed segmentation system for retinal blood vessels in OCTA scans.
Figure 3A:
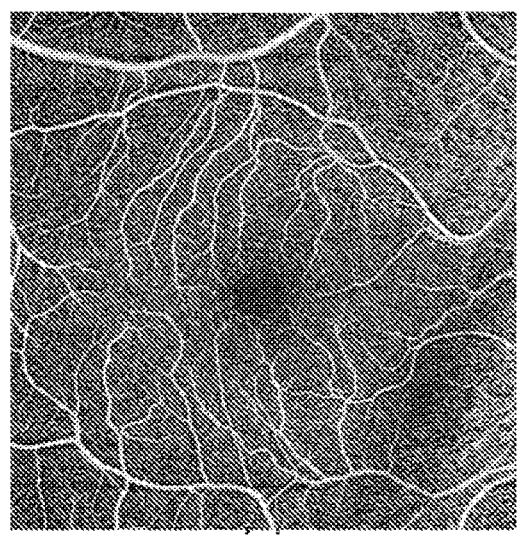
FIG. 3 depicts the step-by-step blood vessels segmentation to retinal superficial map for mild DR patient: (a) the original image, (b) the output of LCDG, (c) the smoothed image after applying GGMRF, (d) the prior intensity model, (e) the joint MGRF segmentation, (f) the final segmentation.
Figure 3B:
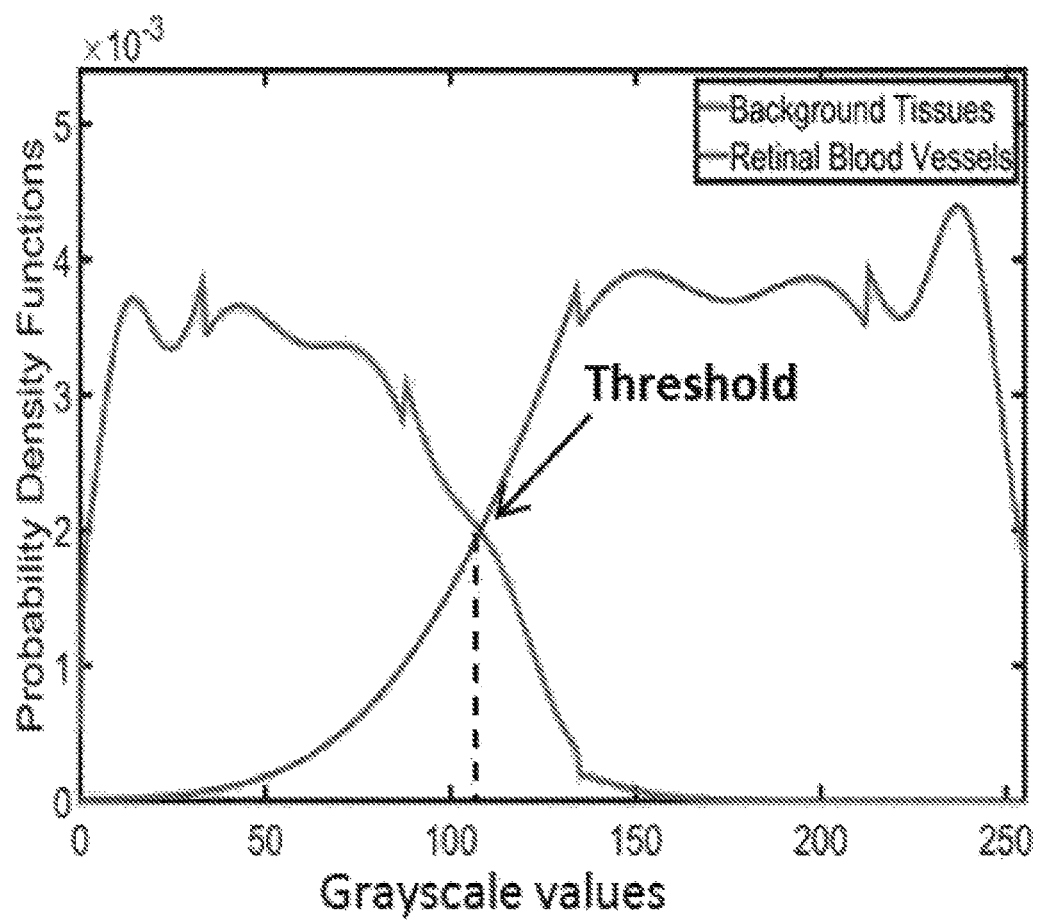
Figure 3C:
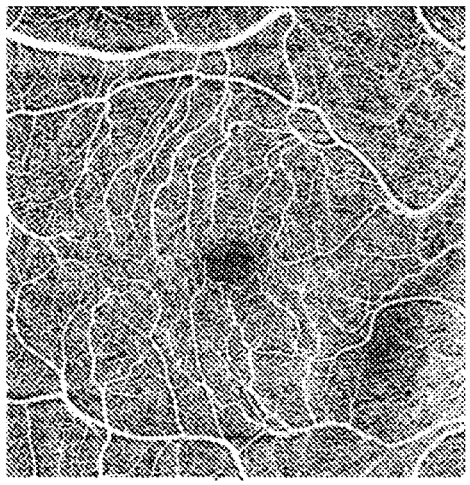
Figure 3D:
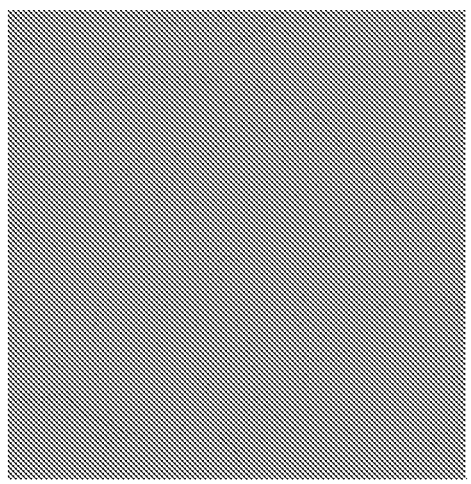
Figure 3E:
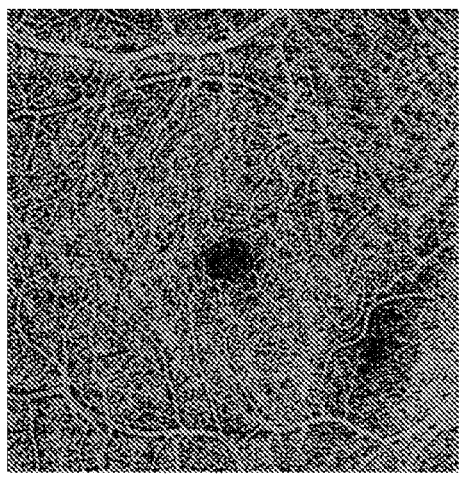
Figure 3F:
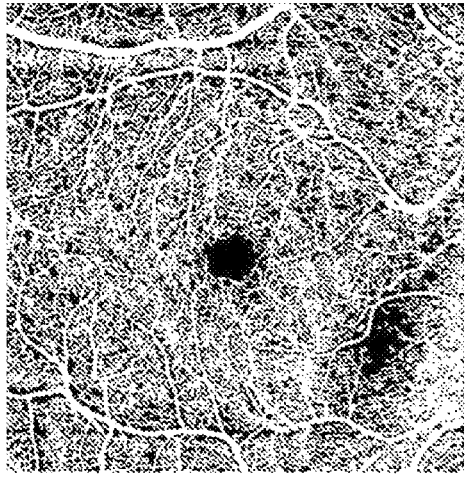

Algorithm 1 describes the main steps of the proposed segmentation technique. FIG. 2 shows the main steps in schematic form and FIG. 3 shows the step by step illustration of the main stages of the proposed segmentation technique.

Algorithm 1—the Proposed Segmentation System
Input: OCTA superficial and deep maps (10)
Training data: OCTA superficial and deep maps manually labeled by experts (12)
1. Preprocessing (14)—Noise Reduction & Contrast Improvement:
  Apply RDHE to adaptively enhance the contrast (16).
  Use LCDG to calculate an initial threshold value (18).
  Smooth the image by applying 2D GGMRF (20).
2. Initial Segmentation (22)—A Joint MGRF Image Model:
  Create the prior intensity model ($P_{Pr}(m)$) from the training data (24).
  Create the current intensity model (P(g|m)) by applying LCDG (26).
  Create the spatial higher order Markov-Gibbs random field (HO-MGRF) model ($P_{GV}(m)$) to enhance the overall accuracy of the data (28).
  Generate the joint Markov-Gibbs random field (MGRF) model (P(g,m)=P(g|m)$P_{Pr}(m)P_{GV}(m)$) (30).
3. Refinement (32)—Final Segmentation:
  Label the result by applying the NB classifier (34).
  Apply the connectivity analysis for the result to create the final segmentation (36).

The preprocessing stage is responsible for the noise reduction and contrast improvement for the OCTA images. The initial segmentation stage includes an integration of three different segmentation models, which are the prior intensity model, which is generated from a set of training images that are manually labeled by one or more experts, the current intensity model, which is based on a modified version of the Expectation Maximization (EM) technique, and the higher-order spatial model, which is based on a MGRF model. The HO-MGRF model is used in addition to the 1st order intensity model to consider the spatial information in order to overcome the low contrast between blood vessels and other tissues. Initial segmentation is obtained using a joint Markov-Gibbs model that integrates all three models. The refining stage produces a final segmentation by applying a Naïve Bayes (NB) classifier for labeling and analyzing the connected components to refine segmentation results.

Preprocessing—RDHE and GGMRF

The preprocessing stage is designed to reduce the noise effect (remove inconsistency) and to improve the contrast of the OCTA images. Initially, OCTA signals (gray levels) are uniformly distributed across the OCTA images. To achieve this, the regional dynamic histogram equalization (RDHE) is applied. The image is divided into blocks of x rows by y columns. Then, dynamic histogram equalization is applied for each block to adaptively enhance the distribution of the gray levels. Therefore, the histogram is remapped by each block, and the pixel's value is adapted to its location in the histogram of the block.

Secondly, to improve the contrast of the OCTA images, a new approach was developed that integrates adaptive estimation of the threshold and the Generalized Gauss-Markov random field (GGMRF) model. An initial gray level threshold that separates the blood vessels from the background is calculated by using the linear combination of discrete Gaussian (LCDG) model with negative and positive discrete Gaussian components. The mixed empirical 1D distribution of OCTA pixels is separated into two distinct components, which are the vessels and background components. This is followed by a refinement step to smooth the input OCTA image to avoid unwanted distortions and noise by utilizing the GGMRF model. GGMRF is an iterative energy minimization method in which the re-estimations are considered as measurements samples. The continuity is amplified by utilizing its maximum A posteriori (MAP) estimates using the pixels 8-neighborhood.

Figure 4:
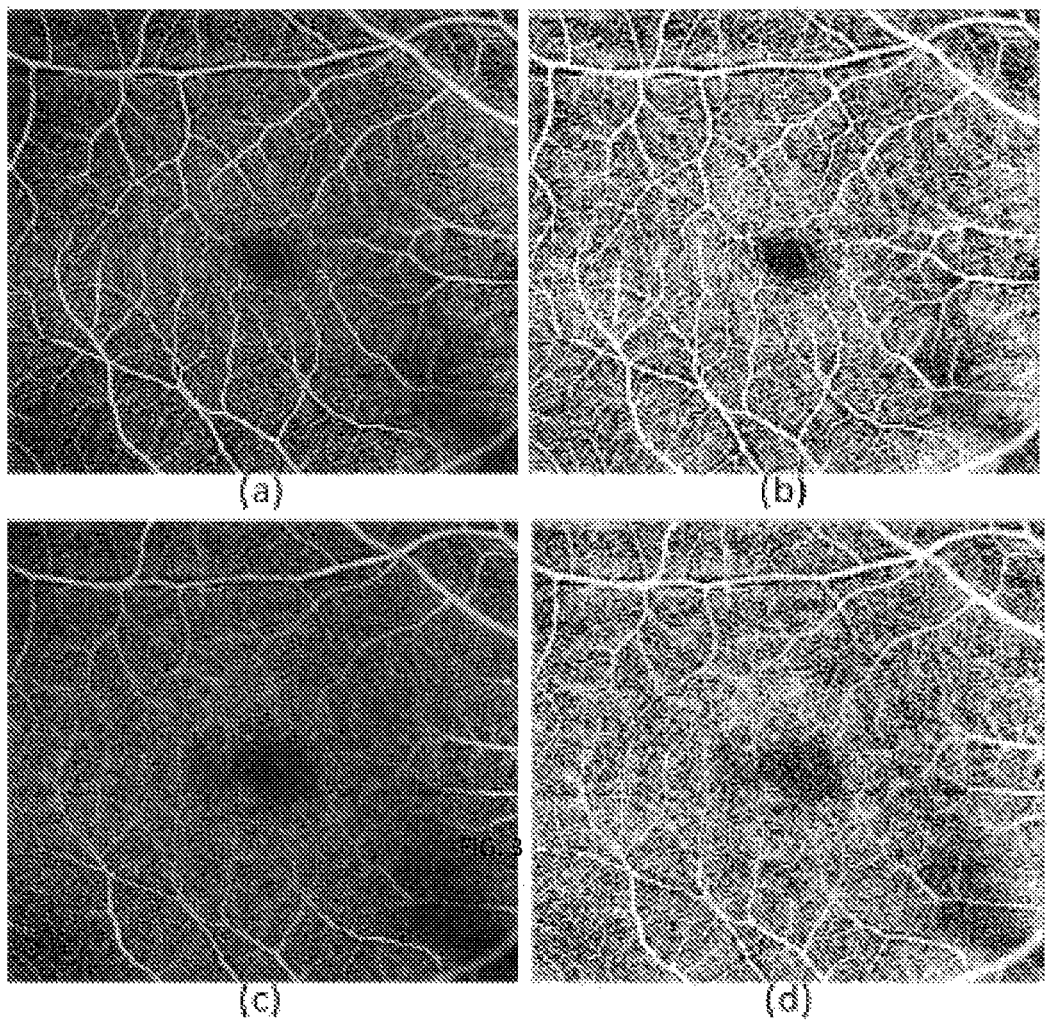
FIG. 4 depicts the result of the GGMRF model for a DR case: (a) the original retinal superficial map, (b) the smoothed retinal superficial map, (c) the original retinal deep map, and (d) the smoothed retinal deep map.

At the 2D location s(i,j), a gradient descent optimization is used to calculate the MAP estimator ($\hat{x}_s$) of the gray level value ($x_s$) utilizing the 2D GGMRF, as shown in Equation 1 below:

$$\hat{x}_s = \underset{\tilde{x}_s}{\operatorname{argmin}}\left\{|x_s - \tilde{x}_s|^\alpha + \rho^\alpha \lambda^\beta \sum_{r\in N}\eta_{s,r}|x_s - \tilde{x}_s|^\beta\right\} \quad (1)$$

where $\tilde{x}_s$ is the neighbors of xs. The parameter $\alpha \in \{1, 2\}$ calculates the Gaussian, which has a value equals to 2 for prior distribution of the estimator. The parameter $\beta \in [1.01, 2.0]$ cogs the smoothing level, which has a value of 1.01. The parameter $\eta s,r$ is the GGMRF potential that is equal to 1.414. The parameters $\rho$ and $\lambda$ are the scaling factors, which have the values 1.0 and 5.0, respectively. The previous values of the parameters are used to increase the homogeneity of the images and to keep the edges. Finally, the calculated MAP estimator is supplied as a smoothed input to the initial segmentation stage. FIG. 4 shows the original and smoothed images by the GGMRF model for both the superficial and deep maps for a DR case, respectively.

Initial Segmentation—the Joint MGRF Model (P(g,m))

A smoothed OCTA image (g) and its map (m) are depicted using a joint probability model (P(g,m)), which integrates three different probability models. First, the $P_{Pr}(m)$ represents the prior gray information that is generated from a set of training data, which are gathered from various subjects and manually labeled by experts. For the data depicted herein, the prior gray information was labeled by three experts. Second, the P(g|m) model presents a conditional distribution of all images. It approximates the marginal gray level probability distributions of the vessels and the background tissues. Finally, the $P_{GV}(m)$ model is a Gibbs probability distribution with potentials V. It identifies the HO-MGRF of spatiality homogeneous maps m. These models are described below in more detail.

Prior Intensity Model ($P_{Pr}(m)$):

This model is created from training data for a set of OCTA images. It uses the gray intensity information of the OCTA images and the Euclidean distance measure. To estimate $P_{Pr}(m)$, a database for a set of manually labeled images of the two image classes (vessels and background) is established by using the gray level values. For each class i, a matrix $M_i$ is constructed by aggregating all the gray values of the pixels of that class from all training images. For each pixel p in the tested gray image, the Euclidean distances $d_{p,i}$ between p and all training matrices $M_i$ are calculated. For each class i, the total number of pixels N are calculated, which are at distances lower than a predefined threshold T. Finally, $P_{Pr}(m)$ for each class is determined with respect to the total number of pixels in the processed image. This Prior Intensity Model is generally known to skilled individuals in the field of medical imaging.

Current Intensity Model P(g|m):

The main purpose of this model is to precisely approximate the marginal gray level probability distributions of the vessels and the non-vessels (background) or P(g|m). Here, the P(g|m) is precisely approximated using the LCDG model of the conditional marginal signal distribution, which is built on an enhanced version of the EM algorithm. This model fits the discrete empirical distribution better than other conventional Gaussian densities. The LCDG model of (P(g|m)) of the intensity distribution has positive (Cp) and negative (Cn) discrete Gaussian (DS), as shown in Equations 2 and 3 below:

$$P(g \mid m) = P(g) = \sum_{r=1}^{C_p} w_{p,r} \psi(q \mid \theta_{p,r}) - \sum_{l=1}^{C_n} w_{n,l} \psi(q, \theta_{n,l}) \quad (2)$$

$$\psi(q \mid \theta) = \Phi_\theta(q + 0.5) - \Phi_\theta(q - 0.5) \quad (3)$$

where $q \in Q = 1, 2, \ldots, Q$ and $\Sigma_{q=1}^{Q} f(q) = 1$. The term $\phi_\theta(q)$ is the cumulative Gaussian probability function with a shorthand notation $\theta = (\mu, \sigma^2)$ for its mean ($\mu$) and variance ($\sigma^2$). The weights ($w_p$ and $w_n$) are non-negative values and their sum is equal to one.

Higher-order Spatial $P_{GV}(m)$ Model:

In addition to the current and prior intensity models, the spatial relationships of the OCTA images are considered. We employed an HO-MGRF model $P_{GV}(m)$ to enhance the overall accuracy of OCTA image and account for the inhomogeneity of the images' gray level. It describes the spatial interactions between the OCTA data pixels. This higher-order model adds to the traditional pairwise cliques the families of the triple and quad cliques. Let $C_a$ denote a family of a-order cliques of an interaction graph. This graph is constructed with nodes in the 2D lattice sites p=(i,j) and edges that connect the interacting sites. The label interactions are modeled by a spatially homogeneous MGRF with up to fourth-order interactions over the nearest 8-neighborhood pixels, as shown in Equation 4 below:

$$P_{GV}(m) = \frac{1}{Z_V} \exp\left(\sum_{a=1}^{A} \sum_{c \in C_a} V_a(m(i, j) : (i, j) \in c\right) \quad (4)$$

where $Z_V$ is the partition function that normalizes the probabilities. The parameter A is the clique families that describe the graph interactions. Finally, $V = [V_a: \{0, \ldots, L\} \to (-\infty, \infty): a=1, \ldots, A]$ is a collection of Gibbs potential functions $V_a$ for the families $C_a$.

Finally, the joint MGRF model P(g,m) is calculated by multiplying the three resulting models. As mentioned previously, these three models are the prior gray intensity model ($P_{Pr}(m)$), the first order intensity model (P(g|m)), and the HO-MGRF model ($P_{GV}(m)$), as shown in Equation 5 below:

$$P(g,m) = P_{Pr}(m) P(g \mid m) P_{GV}(m) \quad (5)$$

Refinement

This stage is responsible for generating the final segmentation result. It has two main steps, which are labeling and connectivity analysis. For the labeling step, the NB classifier is applied to the resulting joint MGRF model to label each pixel in the processed image. NB estimates the class of each pixel (k=1, 2, . . . , K) in the image depending on the maximum probability value, as shown in Equation 5 below:

$$C_{NB} = \underset{k \in \{1,2,\ldots,K\}}{\mathrm{argmax}} \, P(g, m)_k \quad (6)$$

Where K represents the total number of pixels in the image. $P(g,m)_k$ is the joint MGRF probability of the current processed pixel (k). Therefore, the value of $C_{NB}$ indicates the label of each pixel in the image whether it is a vessel or background pixel.

The final segmentation is generated by applying the connectivity analysis to the labeled data to enhance the connectivity of the segmented blood vessels. An 8-connected neighborhood is used herein for each tested pixel. First, all pixels in the image are scanned and assigned a label that is generated from the last step. Then, the equivalence class is resolved by using union-find algorithm. Finally, the pixels are relabeled depending on the resolved equivalence. Therefore, the result is the final segmentation of the retinal blood vessels from the OCTA scans.

Experiment

The proposed blood vessel segmentation system was tested on 47 data sets (23 data sets for normal cases and 24 data sets for mild DR cases). The images were captured from a ZEISS AngioPlex OCT Angiography machine, a vascular imaging platform that provides non-invasive images of blood flow in the eye. The AngioPlex OCT Angiography machine generates six various maps of blood vessels in addition to B-scan flow. These maps are retinal VRI, superficial, deep, avascular, choroid, and choriocapillaris. We conducted our proposed segmentation system on the retinal superficial and deep maps with size 1024×1024. OCTA was performed on 6×6 mm² sections centered on the fovea. The segmentation method was trained on 32 data sets and tested on 15 data sets.

The performance of the proposed system was evaluated by using three various metrics, the absolute vessels volume difference (VVD), the Dice similarity coefficient (DSC), and the area under the ROC curve (AUC).

VVD is the relative absolute vessel difference between the results of the tested model and the ground truth (GT) segmentations. The DSC measures relative correspondence between two areas regarding their true/false positive and negative parts. The lower the value of VVD and the higher the values of DSC and AUC, the more accurate the blood vessel segmentation. DSC, VVD, and AUC are calculated by using Equations 7, 8, and 9, respectively, with Equations 10 and 11 informing Equation 9.

$$DSC = \frac{2TP}{FP + 2TP + FN} \quad (7)$$

$$VVD = 100 \times \frac{Segmentation Area - GT\ Area}{GT\ Area} \quad (8)$$

$$AUC = \frac{Sensitivity + Specificity}{2} \quad (9)$$

$$Sensitivity = \frac{TP}{TP + FN} \quad (10)$$

$$Specificity = \frac{TN}{TN + FP} \quad (11)$$

where TP is the true positive value that indicates the total number of correctly classified pixels of the blood vessels. TN is the true negative value that presents the correctly classified pixels of the background. FP is the false positive value that indicates the total number of the misclassified pixels of the background. FN is the false negative value that represents the total number of the misclassified pixel of the blood vessels.

The metrics were evaluated by comparing the results of our proposed system to the GT information that was generated and labeled by three different retina experts. The segmentation system disclosed herein was compared with three other segmentation systems, which are Soares et al. (J. V. B. Soares, J. J. G. Leandro, R. M. Cesar, H. F. Jelinek, M. J. Cree, Retinal vessel segmentation using the 2-d gabor wavelet and supervised classification, IEEE Transactions on Medical Imaging 25 (9) (2006) 1214-1222), Nguyen et al. (U. T. Nguyen, A. Bhuiyan, L. A. Park, K. Ramamohanarao, An effective retinal blood vessel segmentation method using multi-scale line detection, Pattern Recognition 46 (3) (2013) 703-715), and Azzopardi et al. (G. Azzopardi, N. Strisciuglio, M. Vento, N. Petkov, Trainable {COSFIRE} filters for vessel delineation with application to retinal images, Medical Image Analysis 19 (1) (2015) 46-57).

Figure 5:
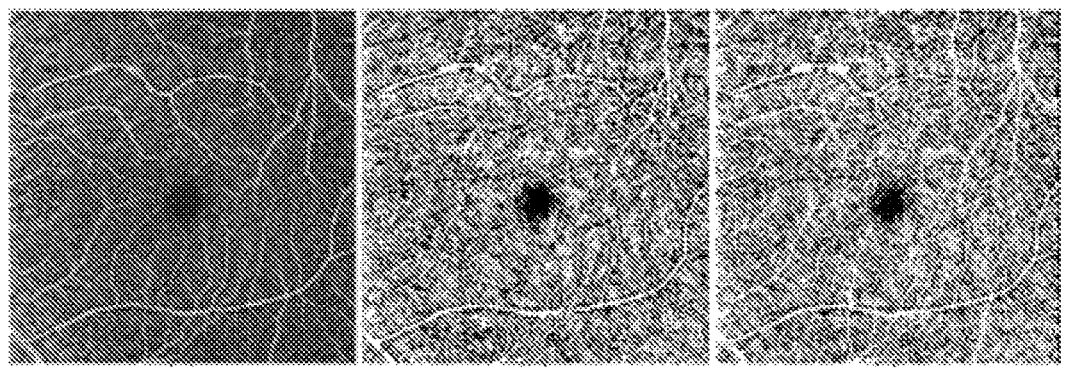
FIG. 5 depicts an example of superficial map segmentation for normal case: (a) the original image, (b) the ground truth, (c) the Soares et al. output, (d) the Nguyen et al. output, (e) the Azzopardi et al. output, (f) the proposed segmentation system output.
Figure 5:
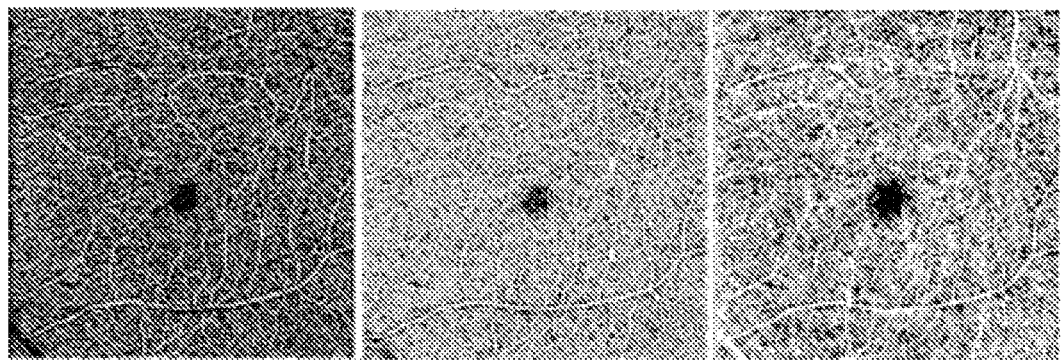
Figure 6:
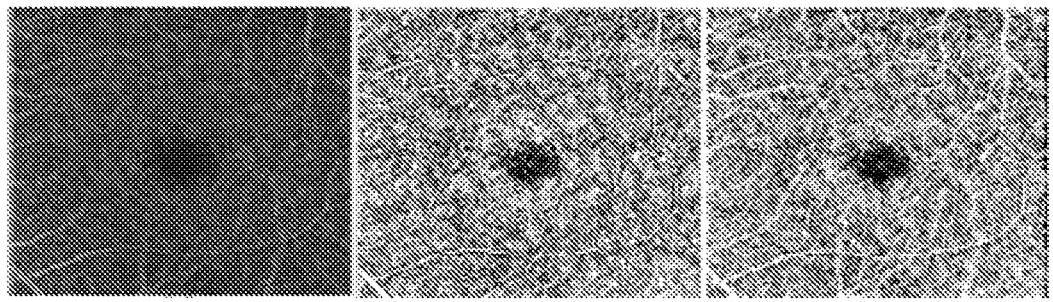
FIG. 6 depicts an example of deep map segmentation for normal case: (a) the original image, (b) the ground truth, (c) the Soares et al. output, (d) the Nguyen et al. output, (e) the Azzopardi et al. output, (f) the proposed segmentation system output.
Figure 6:
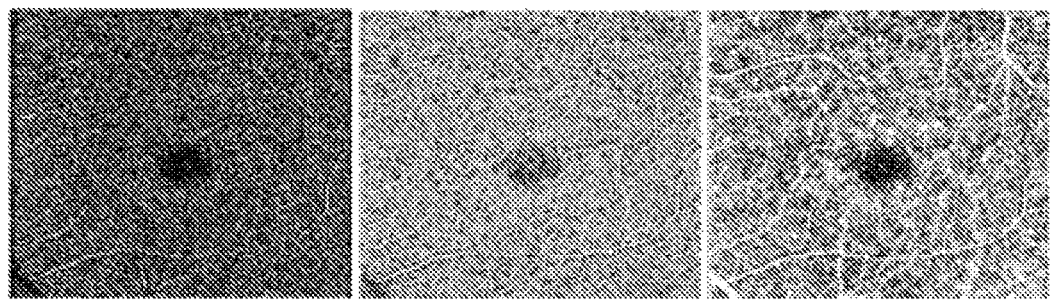
Figure 7:
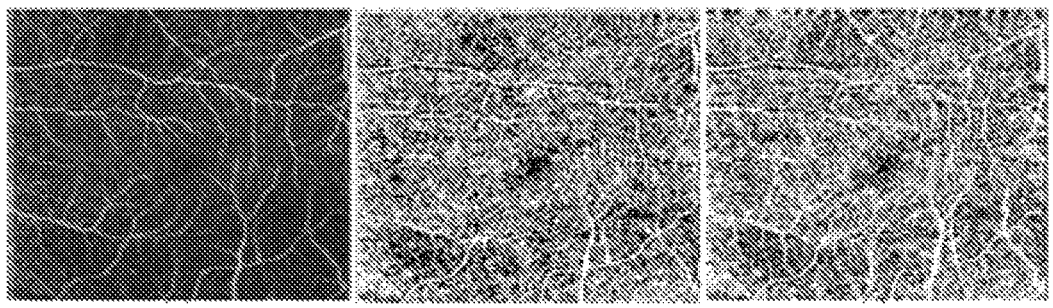
FIG. 7 depicts an example of superficial map segmentation for mild DR case: (a) the original image, (b) the ground truth, (c) the Soares et al. output, (d) the Nguyen et al. output, (e) the Azzopardi et al. output, (f) the proposed segmentation system output.
Figure 7:
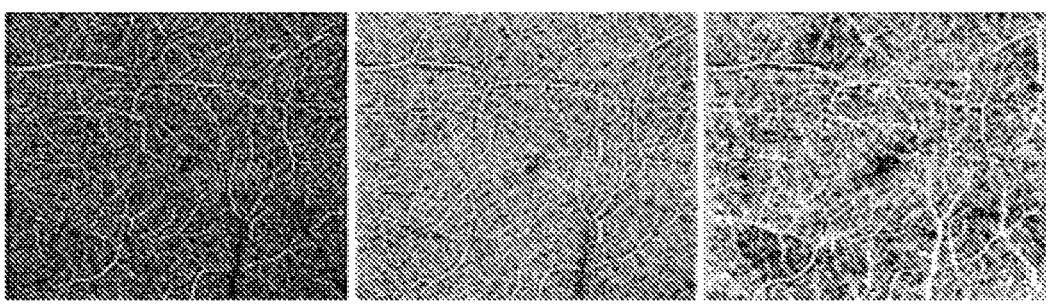
Figure 8:
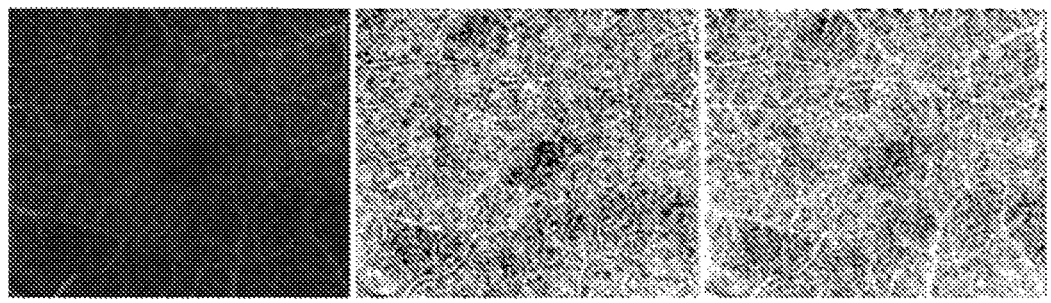
FIG. 8 depicts an example of deep map segmentation for mild DR case: (a) the original image, (b) the ground truth, (c) the Soares et al. output, (d) the Nguyen et al. output, (e) the Azzopardi et al. output, (f) the proposed segmentation system output.
Figure 8:
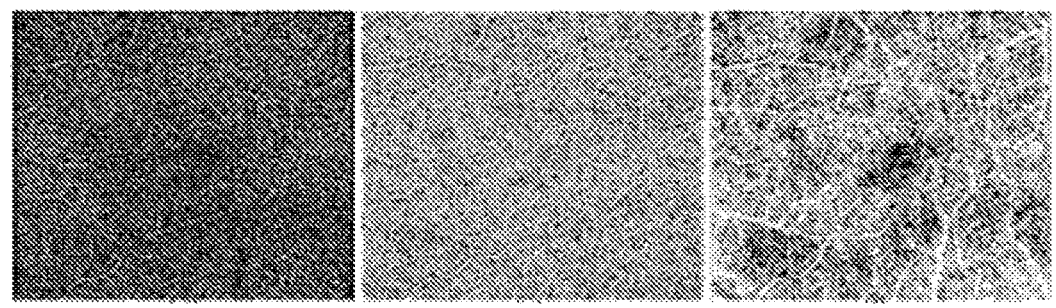

FIG. 5 shows an example of the segmentation process of the retinal superficial map for a normal case. It illustrates the original image, the GT, and the segmentation outputs for all tested systems in addition to the result of our proposed system. Table 1 lists the average results of DSC, VVD, and AUC for all tested segmentation systems. Similarly, FIGS. 6, 7, and 8 show examples of blood vessel segmentation of a retinal deep map for a normal case, a superficial map for a mild DR case, and a deep map for a mild DR case, respectively. Tables 2, 3, and 4 list the average results of DSC, VVD, and AUC for all tested segmentation systems of a retinal deep map for a normal case, a superficial map for a mild DR case, and a deep map for a mild DR case, respectively.

TABLE 1

The comparative segmentation accuracy for the superficial map for the normal cases.

| Tested Systems | DSC | VVD | AUC |
| --- | --- | --- | --- |
| Soares et al. | 0.8036 ± 0.0060 | 0.3564 ± 0.0350 | 0.8225 ± 0.0032 |
| Nguyen et al. | 0.6917 ± 0.0039 | 0.0585 ± 0.0243 | 0.6923 ± 0.0038 |
| Azzopardi et al. | 0.7762 ± 0.0065 | 0.3625 ± 0.0523 | 0.7951 ± 0.0060 |
| Proposed System | 0.9541 ± 0.0032 | 0.0911 ± 0.0066 | 0.9559 ± 0.0031 |

TABLE 2

The comparative segmentation accuracy for the deep map for the normal cases.

| Tested Systems | DSC | VVD | AUC |
| --- | --- | --- | --- |
| Soares et al. | 0.8193 ± 0.0099 | 0.3243 ± 0.0499 | 0.8357 ± 0.0061 |
| Nguyen et al. | 0.6975 ± 0.0054 | 0.0418 ± 0.0308 | 0.6980 ± 0.0051 |
| Azzopardi et al. | 0.7899 ± 0.0125 | 0.3553 ± 0.0482 | 0.8084 ± 0.0098 |
| Proposed System | 0.0911 ± 0.0066 | 0.0681 ± 0.0148 | 0.9640 ± 0.0055 |

TABLE 3

The comparative segmentation accuracy for the superficial map for the mild DR cases.

| Tested Systems | DSC | VVD | AUC |
| --- | --- | --- | --- |
| Soares et al. | 0.8002 ± 0.0093 | 0.3681 ± 0.0516 | 0.8201 ± 0.0051 |
| Nguyen et al. | 0.6885 ± 0.0040 | 0.0648 ± 0.0326 | 0.6893 ± 0.0039 |

TABLE 3-continued

The comparative segmentation accuracy for the superficial map for the mild DR cases.

| Tested Systems | DSC | VVD | AUC |
| --- | --- | --- | --- |
| Azzopardi et al. | 0.7710 ± 0.0091 | 0.3794 ± 0.0681 | 0.7914 ± 0.0079 |
| Proposed System | 0.9511 ± 0.0107 | 0.0972 ± 0.0136 | 0.9531 ± 0.0101 |

TABLE 4

The comparative segmentation accuracy for the deep map for the mild DR cases.

| Tested Systems | DSC | VVD | AUC |
| --- | --- | --- | --- |
| Soares et al. | 0.8248 ± 0.0181 | 0.2983 ± 0.1245 | 0.8403 ± 0.0136 |
| Nguyen et al. | 0.7004 ± 0.0103 | 0.0777 ± 0.0672 | 0.7027 ± 0.0137 |
| Azzopardi et al. | 0.7972 ± 0.0197 | 0.2677 ± 0.1169 | 0.8096 ± 0.0146 |
| Proposed System | 0.9335 ± 0.0425 | 0.0842 ± 0.0246 | 0.9351 ± 0.0419 |

Soares et al. introduced a segmentation system that is based on 2D Gabor wavelet transform and pixel's intensity. They are presented as a feature vector that is taken at multi-scales for the retinal blood vessels images. The authors used a Bayesian classifier with class conditional probability density functions, which are described as Gaussian mixtures, to achieve a fast classification. The Soares et al. system was tested on the OCTA data sets to compare it with the novel system disclosed herein. The Soares et al. system achieved accuracy ratings of 81.19±1.08% for DSC, 33.67±6.52% for VDD, and 82.97±0.70% for AUC in average for all tested data sets. The most of the differences between the results of this system and the GT lie on the boundaries of the image.

Nguyen et al. proposed a blood vessel segmentation technique that is based on the linear combination of line detectors at different scales. The Nguyen et al. technique was tested on the OCTA data sets and it achieved 69.45±0.59% for DSC, 6.07±3.87% for VDD, and 69.56±0.66% for AUC in average for all tested data sets. The segmented blood vessels contained many discontinuities. In addition, the results of the retinal deep map lose many details of vessels.

Azzopardi et al. implemented an automatic retinal blood vessel segmentation system based on the B-COSFIRE filter. It calculated the weighted geometric mean of the result of Difference of Gaussian (DoG) filters to obtain orientation selectivity. In addition, its supports were aligned in a collinear manner. This system was tested on the OCTA data sets, and it achieved 78.33±1.19% for DSC, 34.12±7.13% for VDD, 80.11±0.96% for AUC and in average for all tested data sets. The segmented blood vessels contained many discontinuities. In addition, some large vessels were classified as background, as shown in FIG. 7.

In comparison the retinal blood vessel segmentation system disclosed herein achieved 95.04±3.75% for DSC, 8.51±1.49% for VDD, 95.20±1.52% for AUC in average for all tested data sets. The results reflect the high accuracy of the proposed system and show that the system outperforms the other tested systems.

Figure 9:
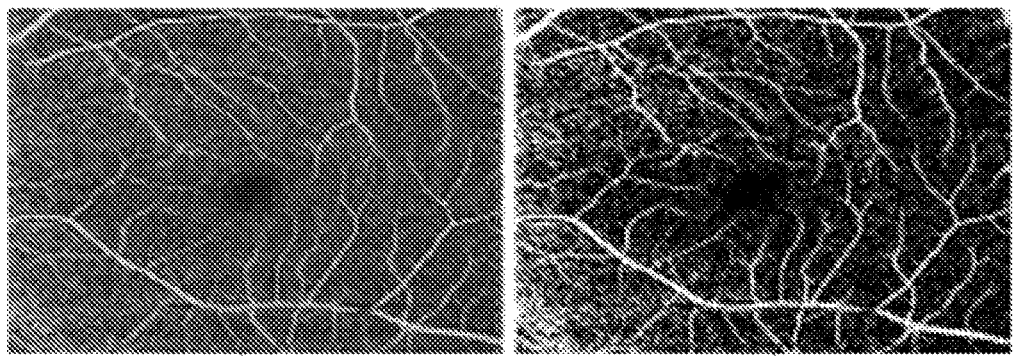
FIG. 9 depicts (a) an original OCTA image, (b) the image resulting from the disclosed segmentation methods absent RDHE and GGMRF preprocessing, and (c) the image resulting from the disclosed segmentation method with RDHE and GGMRF preprocessing.
Figure 9:
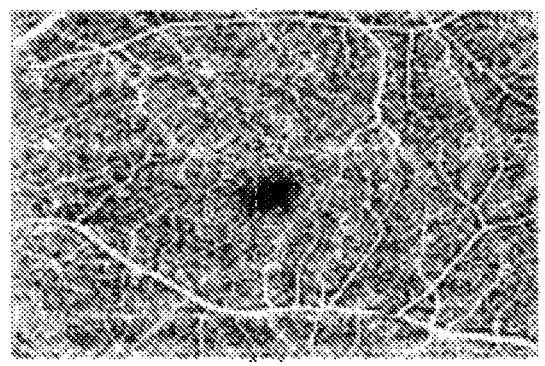

To highlight the importance of applying RDHE and GGMRF models, FIG. 9 displays the results of performing the disclosed segmentation approach on OCTA images with and without these models. FIG. 9(*a*) shows the original image, FIG. 9(*b*) shows the image without applying RDHE and GGMRF models, and FIG. 9(*c*) shows the image with applying RDHE and GGMRF models. The image without RDHE and GGMRF models achieved 54.56% for DSC, 58.33% for VVD, and 56.71% for AUC. The image with RDHE and GGMRF achieved 96.04% for DSC, 7.95% for VVD, and 96.18% for AUC. In addition, the most of the small vessels are lost in the segmented image (FIG. 9(b)) without the enhancing stage.

Feature Extraction and Diagnosis

In some embodiments, a computer aided diagnostic (CAD) system performs the above-described segmentation processes, and extracts retinal features correlated with a specific disease state. These extracted retinal features are fed into a support vector machine (SVM) classifier with radial basis function (RBF) kernel to detect changes in the retinal vasculature, which classifies patients as being either normal state or disease state based on the extracted retinal features. The SVM classifier is a supervised learning model, a machine learning technique that analyzes data for classification based on a set of training examples (e.g., OCTA images manually labeled as normal state or diabetic retinopathy state), and builds a model to assign new examples to one category or the other. In an exemplary embodiment, the feature extraction stage extracts the local density of retinal blood vessels, the caliber of retinal vessels, and the size of the foveal avascular zone (FAZ), each of these features having pathophysiological relevance to DR.

The diagnosis of DR required a detailed analysis of the vasculature to track pathological changes in the retinal vasculature. We calculated the local density of blood vessels in both superficial and deep retinal maps to capture these changes. A Parzen window technique was used to estimate the local vascular density. This technique was implemented to estimate the density probability distribution p(r) of blood vessels from the segmented OCTA images in specific window size. To ensure that the system was not sensitive to size of the window, the density of the blood vessels was estimated using a sequence of Parzen window sizes (3×3, 5×5, 7×7, 9×9 and 11×11 pixels). Blood vessel densities for each window were represented as a cumulative distribution function (CDF) (F($r_c$)). CDF is the probability of the variable that takes a value less than or equal to $r_c$, as represented by the equation Fr($r_c$)=P(r≤$r_c$). The resulting CDFs are used as discriminatory features, which were fed to the SVM classifier to diagnose the processed images as either being normal state or DR.

The second extracted feature set from the segmented OCTA scans was the diameter, often referred to as the "size" or "caliber," of the retinal vessels. The goal of this feature extraction is to distinguish large and small blood vessels depending on the appearance and intensity level of the vessels.

Figure 10:
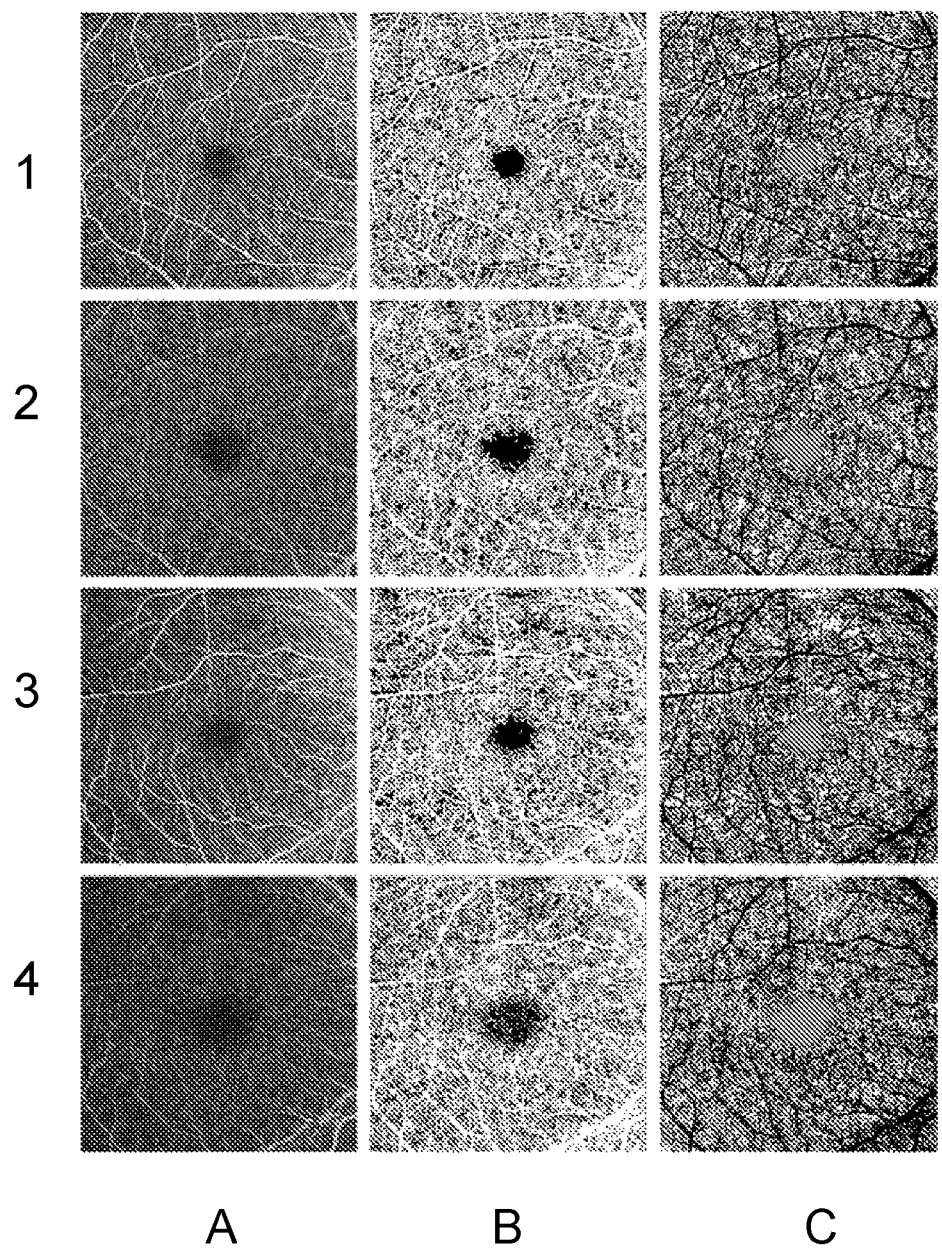
FIG. 10 depicts FAZ areas for normal and mild DR cases. Row 1 depicts superficial maps for normal cases. Row 2 depicts deep maps for normal cases. Row 3 depicts superficial maps for mild DR cases. Row 4 depicts deep maps for mild DR cases. Column A depicts original OCTA images. Column B depicts images after segmentation according to the method disclosed herein. Column C depicts the extracted FAZ areas.

The third feature extracted was the diameter, often referred to as the "size," of the FAZ. An enlargement of the zone is usually found in patients with DR because of the loss of capillaries in the perifoveal capillary network. FIG. 10 depicts original OCTA images, images segmented according to the disclosed method, and the extracted FAZ areas for superficial and deep maps, and for normal case and mild DR case patients. After extracting the FAZ, the distance map was calculated to represent the segmented area as a local feature.

The final stage in the proposed CAD system was the diagnosis stage, which is responsible for the classification of OCTA images into mild DR and normal cases. This stage was based on the three aforementioned extracted features, the local density of retinal blood vessels, the caliber of retinal vessels, and the size of the FAZ. The diagnosis stage was trained and tested on five different combinations features: individual CDF curves of blood vessel density of the superficial or deep retinal plexuses; the combined CDF curves from both superficial and deep retinal plexuses; the combined CDFs for vessel density from both plexuses plus vessel calibre; the combined CDF curves from both plexuses plus FAZ size; and the combined CDFs from both plexuses plus vessel calibre plus FAZ size. The proposed CAD system employed the SVM with RBF kernel technique to classify the OCTA images.

The performance of the proposed CAD system was evaluated using five different metrics: accuracy (ACC), sensitivity, specificity, area under the ROC curve (AUC) and the dice similarity coefficient (DSC). ACC is defined as ACC=(TP+TN)/(TP+TN+FP+FN), where TP is true positives, TN is true negatives, FP is false positives, and FN is false negatives. The gold standard, or 'ground truth', for determining accuracy of each diagnosis made by the CAD system was the clinical diagnosis made by the patient's attending retinal specialist on examination. Three cross-validation techniques were used, specifically, leave one subject out (LOSO), twofold cross-validation and fourfold cross-validation. In addition, the system compared our proposed system with five different state-of-the-art classifiers, which are SVM with linear kernel, SVM with polynomial kernel, K-nearest neighbor (KNN), classification tree and random forest techniques.

The CAD system was trained and tested on 530 images from 106 patients (23 datasets for normal cases and 83 datasets for mild DR cases). Average age of subjects was 62 years (range 31-79 years, SD 17.2), 53% were women and all were DMII. Nine subjects were excluded due to poor quality images that could not be analysed. In 52 patients, we had full access to complete medical histories and laboratory values. Among these 52 patients, the mean duration of diabetes was 11 year (range 0-26 years, SD 6.3), mean haemoglobin A1c was 8.9% (range 6.1-13.4, SD 2.4), prevalence of systemic hypertension was 84% and prevalence of hyperlipidaemia was 69%.

The CAD system (using the SVM classifier with RBF kernel) achieved the greatest accuracy as compared with other classifiers. In addition, Parzen window of size 11×11 produced superior results over smaller window sizes. When using the superficial retinal map alone, accuracy was 80.0%, sensitivity 87.2%, specificity 65.2%, AUC 76.2% and DSC 85.4%. Using the deep retinal map alone produced superior results to that of the superficial map. Its accuracy was 91.4%, sensitivity 95.7%, specificity of 82.6%, AUC 89.2% and DSC 93.8%. The best results were achieved when blood vessel density of the superficial retinal plexus was combined with that of the deep retinal plexus, the size of the FAZ for both plexuses and vessel caliber for both plexuses. When all of these features were combined, accuracy was 94.3% (95% CI 71.4% to 94.3%), sensitivity 97.9% (95% CI 78.7% to 97.9%), specificity 87.0% (95% CI 47.8% to 87%), AUC 92.4% (65.4% to 92.4%) and DSC 95.8% (79.6% to 95.8%).

Table 5 lists the classification results based on the CDFs, which are generated from the blood vessel density, vessel size and the size of the FAZ for both the superficial and deep retinal plexuses. It lists the results of three different validation methods, which are LOSO, twofold and fourfold cross-validation. The best results were achieved by using SVM classifier with RBF kernel in both twofold and fourfold cross-validation.

TABLE 5

Classification results based on the CDFs of blood vessel density, vessel caliber and FAZ size for both the superficial and deep retinal plexuses.

| Classifiers | Validation | ACC (%) | Sens. (%) | Spec. (%) | AUC (%) | DSC (%) |
|---|---|---|---|---|---|---|
| KNN | LOSO | 92.9 | 93.6 | 91.3 | 92.5 | 94.6 |
| KNN | Twofold | 85.7 | 89.4 | 78.3 | 83.8 | 89.4 |
| KNN | Fourfold | 84.3 | 89.4 | 73.9 | 81.6 | 88.4 |
| Classification Tree | LOSO | 90.0 | 95.7 | 78.3 | 87.0 | 92.8 |
| Classification Tree | Twofold | 85.7 | 93.6 | 69.6 | 81.6 | 89.8 |
| Classification Tree | Fourfold | 87.1 | 91.5 | 78.3 | 84.9 | 90.5 |
| RF | LOSO | 81.4 | 83.0 | 78.3 | 87.0 | 92.8 |
| RF | Twofold | 80.0 | 87.2 | 65.2 | 76.2 | 85.4 |
| RF | Fourfold | 82.9 | 85.1 | 78.3 | 81.7 | 87.0 |
| SVM (linear) | LOSO | 90 | 95.7 | 78.3 | 87.0 | 92.8 |
| SVM (linear) | Twofold | 87.1 | 91.5 | 78.3 | 84.9 | 90.5 |
| SVM (linear) | Fourfold | 81.4 | 87.2 | 69.6 | 78.4 | 86.3 |
| SVM (polynomial) | LOSO | 90.0 | 89.4 | 91.3 | 90.3 | 92.3 |
| SVM (polynomial) | Twofold | 87.1 | 89.4 | 82.6 | 86.0 | 90.3 |
| SVM (polynomial) | Fourfold | 87.1 | 91.5 | 78.3 | 84.9 | 90.5 |
| SVM (RBF) | LOSO | 88.6 | 95.7 | 73.9 | 84.8 | 91.8 |
| SVM (RBF) | Twofold | 94.3 | 100 | 82.6 | 91.3 | 95.9 |
| SVM (RBF) | Fourfold | 94.3 | 97.9 | 87.0 | 92.4 | 95.8 |

Various aspects of different embodiments of the present invention are expressed in paragraphs X1 and X2 as follows:

X1. One aspect of the present invention pertains to a method for segmentation of retinal blood vessels comprising providing at least one optical coherence tomography angiography digital image, the image including a plurality of pixels; preprocessing the image, wherein the preprocessing includes calculating a threshold for separating blood vessels from background in the image; segmenting the image, wherein the segmenting includes calculating a probability, based on at least one probability model, that each pixel in the plurality of pixels depicts a blood vessel or background; and refining the segmented image; wherein the refining includes labeling each pixel as depicting either a blood vessel or background based on said probability.

X2. Another aspect of the present invention pertains to a method for diagnosing diabetic retinopathy comprising preprocessing at least one optical coherence tomography angiography digital image for a patient, the image including a plurality of pixels, wherein the preprocessing includes calculating a threshold for separating blood vessels from background in the image; segmenting the images, wherein the segmenting includes calculating a probability, based on at least one probability model, that each pixel in the plurality of pixels depicts a blood vessel or background; refining the segmented image; wherein the refining includes labeling each pixel as depicting either a blood vessel or background based on said probability; extracting retinal features correlated with diabetic retinopathy from the image; and submitting the extracted retinal features to a supervised learning model trained to classify images as normal state or diabetic retinopathy state; wherein the supervised learning model outputs a classification of normal state or diabetic retinopathy state for the patient based on the extracted retinal features.

X3. A further aspect of the present invention pertains to an article of manufacture having one or more non-transitory computer readable storage media storing instructions thereon which, when executed by a computing device, cause the device to perform a method comprising preprocessing an optical coherence tomography angiography digital image, the image including a plurality of pixels, wherein the preprocessing includes calculating a threshold for separating blood vessels from background in the image; segmenting the image, wherein the segmenting includes calculating a probability, based on at least one probability model, that each pixel in the plurality of pixels depicts a blood vessel or background; and refining the segmented image; wherein the refining includes labeling each pixel as depicting either a blood vessel or background based on said probability.

Yet other embodiments pertain to any of the previous statements X1, X2 or X3 which are combined with one or more of the following other aspects.

Wherein the preprocessing further includes uniformly distributing grey levels across each image.

Wherein the preprocessing further includes applying a smoothing factor to improve contrast in the images.

Wherein the preprocessing comprises uniformly distributing grey levels across each image, calculating a threshold for separating blood vessels from background in the images, and applying a smoothing factor to improve contrast in the images.

Wherein the segmenting includes calculating a probability, based on a plurality of probability models, that each pixel in the plurality of pixels depicts a blood vessel or background.

Wherein the segmenting includes calculating a probability, based on a joint probability model generated by combining the plurality of probability models, that each pixel in the plurality of pixels depicts a blood vessel or background.

The method of claim 10, wherein the segmenting includes calculating a probability, based on a joint probability model generated by multiplying a plurality of probability models, that each pixel in the plurality of pixels depicts a blood vessel or background.

Wherein the plurality of probability models include a prior gray intensity model, a first order intensity model, and a higher order Markov-Gibbs random field model.

Wherein the refining further includes, after the labeling, relabeling each pixel as depicting either a blood vessel or background based on equivalence between said pixel and pixels neighboring said pixel.

Wherein the at least one optical coherence tomography angiography digital image is a deep optical coherence tomography angiography digital image and a superficial optical coherence tomography angiography digital image.

Wherein the extracted retinal features are at least one of local density of retinal blood vessels, caliber of retinal vessels, and size of the foveal avascular zone.

Wherein the extracted retinal features are local density of retinal blood vessels, caliber of retinal vessels, and size of the foveal avascular zone.

Wherein the supervised learning model is a support vector machine classifier with radial basis function kernel.

Wherein the retinovascular disease is diabetic retinopathy, and wherein the disease state is diabetic retinopathy state.

The foregoing detailed description is given primarily for clearness of understanding and no unnecessary limitations are to be understood therefrom, for modifications can be made by those skilled in the art upon reading this disclosure and may be made without departing from the spirit of the invention. Although specific spatial dimensions are stated herein, such specific quantities are presented as examples only.

What is claimed is:

1. A method for segmentation of retinal blood vessels comprising:
   providing at least one optical coherence tomography angiography digital image, the image including a plurality of pixels;

preprocessing the image, wherein the preprocessing includes calculating a threshold for separating blood vessels from background in the image;

segmenting the image, wherein the segmenting includes calculating a probability, based on at least one probability model, that each pixel in the plurality of pixels depicts a blood vessel or background; and refining the segmented image;

wherein the refining includes labeling each pixel as depicting either a blood vessel or background based on said probability and, after the labeling, relabeling each pixel as depicting either a blood vessel or background based on equivalence between said pixel and pixels neighboring said pixel.

2. The method of claim 1, wherein the preprocessing further includes uniformly distributing grey levels across each image.

3. The method of claim 1, wherein the preprocessing further includes applying a smoothing factor to improve contrast in the images.

4. The method of claim 1, wherein the preprocessing comprises uniformly distributing grey levels across each image, calculating a threshold for separating blood vessels from background in the images, and applying a smoothing factor to improve contrast in the images.

5. The method of claim 1, wherein the segmenting includes calculating a probability, based on a plurality of probability models, that each pixel in the plurality of pixels depicts a blood vessel or background.

6. The method of claim 5, wherein the segmenting includes calculating a probability, based on a joint probability model generated by combining the plurality of probability models, that each pixel in the plurality of pixels depicts a blood vessel or background.

7. The method of claim 6, wherein the plurality of probability models include a prior gray intensity model, a first order intensity model, and a higher order Markov-Gibbs random field model.

8. The method of claim 1, wherein the at least one optical coherence tomography angiography digital image is a deep optical coherence tomography angiography digital image and a superficial optical coherence tomography angiography digital image.

9. A method for diagnosing diabetic retinopathy comprising:

preprocessing at least one optical coherence tomography angiography digital image for a patient, the image including a plurality of pixels, wherein the preprocessing includes uniformly distributing grey levels across the image, calculating a threshold for separating blood vessels from background in the image, and applying a smoothing factor to improve contrast in the image;

segmenting the images, wherein the segmenting includes calculating a probability, based on at least one probability model, that each pixel in the plurality of pixels depicts a blood vessel or background;

refining the segmented image; wherein the refining includes labeling each pixel as depicting either a blood vessel or background based on said probability;

extracting retinal features correlated with diabetic retinopathy from the image; and submitting the extracted retinal features to a supervised learning model trained to classify images as normal state or diabetic retinopathy state;

wherein the supervised learning model outputs a classification of normal state or diabetic retinopathy state for the patient based on the extracted retinal features.

10. The method of claim 9, wherein the extracted retinal features are at least one of local density of retinal blood vessels, caliber of retinal vessels, and size of the foveal avascular zone.

11. The method of claim 10, wherein the extracted retinal features are local density of retinal blood vessels, caliber of retinal vessels, and size of the foveal avascular zone.

12. The method of claim 9, wherein the supervised learning model is a support vector machine classifier with radial basis function kernel.

13. The method of claim 9, wherein the segmenting includes calculating a probability, based on a joint probability model generated by combining a plurality of probability models, that each pixel in the plurality of pixels depicts a blood vessel or background.

14. An article of manufacture having one or more non-transitory computer readable storage media storing instructions thereon which, when executed by a computing device, cause the device to perform a method comprising:

preprocessing an optical coherence tomography angiography digital image, the image including a plurality of pixels, wherein the preprocessing includes calculating a threshold for separating blood vessels from background in the image;

segmenting the image, wherein the segmenting includes calculating a probability, based on a joint probability model generated by combining a plurality of probability models, that each pixel in the plurality of pixels depicts a blood vessel or background; and refining the segmented image; wherein the refining includes labeling each pixel as depicting either a blood vessel or background based on said probability.

15. The article of claim 14, wherein the method further comprises extracting retinal features correlated with a retinovascular disease from the image; and submitting the extracted retinal features to a supervised learning model trained to classify images as normal state or disease state;

wherein the supervised learning model outputs a classification of normal state or disease state for the patient based on the extracted retinal features.

16. The article of claim 15, wherein the retinovascular disease is diabetic retinopathy, and wherein the disease state is diabetic retinopathy state.

17. The article of claim 15, wherein the extracted retinal features are at least one of local density of retinal blood vessels, caliber of retinal vessels, and size of the foveal avascular zone.

* * * * *